(12) United States Patent
Hagiwara et al.

(10) Patent No.: US 12,138,253 B2
(45) Date of Patent: Nov. 12, 2024

(54) TUMOR SUPPRESSION

(71) Applicant: Kyoto University, Kyoto (JP)

(72) Inventors: Masatoshi Hagiwara, Kyoto (JP); Masahiko Ajiro, Kyoto (JP); Tetsunori Sakamoto, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 246 days.

(21) Appl. No.: 17/024,435

(22) Filed: Sep. 17, 2020

(65) Prior Publication Data

US 2021/0100781 A1    Apr. 8, 2021

(30) Foreign Application Priority Data

Sep. 17, 2019 (JP) .................. 2019-168668

(51) Int. Cl.
*A61K 31/4409* (2006.01)
*A61P 35/00* (2006.01)

(52) U.S. Cl.
CPC .......... *A61K 31/4409* (2013.01); *A61P 35/00* (2018.01)

(58) Field of Classification Search
CPC ................ A61K 31/4409; A61P 35/00
See application file for complete search history.

(56) References Cited

U.S. PATENT DOCUMENTS

| 2007/0135367 A1 | 6/2007 | Hagiwara et al. |
| 2014/0256705 A1* | 9/2014 | Hasvold ............. A61P 1/18 544/405 |

FOREIGN PATENT DOCUMENTS

| JP | 2019-38755 A | 3/2019 |
| WO | WO 2005/063293 A1 | 7/2005 |
| WO | WO 2009/020198 A1 | 2/2009 |

OTHER PUBLICATIONS

Tanaka et al., "Inhibitory effect of CDK9 inhibitor FIT-039 on hepatitis B virus propagation", Antiviral Research (2016), 133: pp. 156-164 (Year: 2016).*
Xie et al., "Kaposi's Sarcoma-Associated Herpesvirus Infection in Chinese Patients With Chronic Hepatitis B", Journal of Medical Virology (2011), 83: pp. 879-883. (Year: 2011).*
You, J., V. Srinivasan, G. Denis, W. Harrington, M. Ballestas, K. Kaye, and P. Howley, "Kaposi's Sarcoma-Associated Herpesvirus Latency-Associated Nuclear Antigen Interacts with Bromodomain Protein Brd4 on Host Mitotic Chromosomes", J. Virol. (2006), 80(18), pp. 8909-8919. (Year: 2006).*
Ajiro, M., H. Sakai, H. Onogi, M. Yamamoto, E. Sumi, T. Sawada, T. Nomura, K. Kabashima, T. Hosoya and M. Hagiwara, "CDK9 Inhibitor FIT-039 Suppresses Viral Oncogenes E6 and E7 and Has a Therapeutic Effect on HPV-Induced Neoplasia", Clin Cancer Res. (2018), 24(18), pp. 4518-4528. (Year: 2018).*
Tanaka, T., et al., "Inhibitory effect of CDK9 inhibitor FIT-039 on hepatitis B virus propagation", Antiviral Research (2016), 133: pp. 156-164. (Year: 2016).*
Dai, L., M. Zhao, W. Jiang, Z. Lin, L. Del Valle and Z. Qin, "KSHV co-infection, a new co-factor for HPV-related cervical carcinogenesis?", Am J Cancer Res (2018), 8(11), pp. 2176-2184. (Year: 2018).*
Qing et al., "Effects of cyclin-dependent kinase 9 (CDK9) on lytic replication of Kaposi's sarcoma-associated herpesvirus (KSHV)", Zhonghua Weishengwuxue he Mianyixue Zazhi, Chin J Microbiol Immunol, Nov. 2017, vol. 37, No. 11, pp. 810-815.
Sakamoto et al., "Assessment of antiviral effect of FIT-039 against Kaposi's sarcoma-associated herpesvirus", The 66th Annual Meeting of the Japanese Society for Virology, P1-AV-14, Sep. 18, 2018, total of 3 pages.
Tanaka et al., "Inhibitory effect of CDK9 inhibitor FIT-039 on hepatitis B virus propagation", Antiviral Research 133 (2016), pp. 156-164.
Yamamoto et al., "CDK9 inhibitor FIT-039 prevents replication of multiple DNA viruses", The Journal of Clinical Investigation, Aug. 2014, vol. 124, No. 8, pp. 3479-3488.
Japanese Office Action for corresponding Japanese Application No. 2019-168668, dated Aug. 31, 2023.

* cited by examiner

*Primary Examiner* — Amanda L. Aguirre
*Assistant Examiner* — Sagar Patel
(74) *Attorney, Agent, or Firm* — Birch, Stewart, Kolasch & Birch, LLP

(57) ABSTRACT

Provided is a method for preventing, ameliorating, suppressing the progression of, and/or treating a tumor caused by a tumor virus, the method including the step of administering, to a subject, an effective amount of a component that targets a gene product of the tumor virus.

11 Claims, 5 Drawing Sheets

TUMOR SUPPRESSION

CROSS-REFERENCE TO RELATED APPLICATION

This application claims benefit of priority to Japanese Patent Application No. JP2019-168668, filed Sep. 17, 2019, the entire content of which is incorporated herein by reference.

BACKGROUND

1. Field

The present disclosure relates to preventing, ameliorating, suppressing the progression of, and treating, a tumor caused by a tumor virus, and also relates to a pharmaceutical composition to the tumor.

2. Description of Related Art

A virus involved in tumor formation is called a tumor virus or a cancer virus.

As human tumor viruses, the following are known: hepatitis B virus (HBV) and hepatitis C virus (HCV) in hepatocellular carcinoma; Kaposi sarcoma-associated herpesvirus (KSHV) that is associated with Kaposi sarcoma, primary effusion lymphoma (PEL), etc.; human papillomavirus (HPV) in cervical cancer; human T cell leukemia virus (HTLV-1) associated with adult T cell leukemia; Merkel cell polyomavirus (MCV) in Merkel cell cancer; and Epstein-Barr virus (EBV) associated with Burkitt's lymphoma, etc.

Human papillomavirus (HPV) is a DNA virus that belongs to Papillomaviridae and has a circular double-strand DNA as a genome. HPV spreads through contagion. HPV infects epithelial or mucous membranes, causes E6 protein and E7 protein, as HPV nonstructural protein, to be expressed in the infected host cells, and decomposes tumor suppressor genes such as the p53 gene and the pRB gene in the host cells, thereby replicating the virus.

SUMMARY

Kaposi sarcoma-associated herpesvirus (KSHV) is a virus that was found in a Kaposi sarcoma as a complication of AIDS, and is called HHV-8 as well. KSHV is a double-strand DNA virus having a large envelope, falling in the category of a γ-2 herpesvirus subfamily (the genus rhadinovirus). It also is involved in the onset of a lymphoproliferative disease such as PEL, besides Kaposi sarcoma.

As a compound that exhibits an antiviral effect against a virus such as the human papillomavirus, N-[5-fluoro-2-(1-piperidinyl)phenyl]-4-pyridinethioamide is known (WO2005/063293, WO2009/020198, and Yamamoto M et al., J Clin Invest, 2014, 124(8), 3479-3488). N-[5-fluoro-2-(1-piperidinyl)phenyl]-4-pyridinethioamide is known to target a phosphorylation enzyme in host cells, suppress the expression of the E6 and E7 genes of HPV, and stabilize the p53 gene, thereby to exhibit the antiviral effect.

The present disclosure provides a pharmaceutical composition to a tumor in which a tumor virus is involved, or a method for treating the same.

The present disclosure, in one aspect, relates to a pharmaceutical composition for preventing, ameliorating, suppressing the progression of, and/or treating, a tumor caused by a tumor virus, the pharmaceutical composition containing a component that targets a gene product of the tumor virus as an active ingredient.

The present disclosure, in another aspect, relates to a method for preventing, ameliorating, suppressing the progression of, and/or treating, a tumor caused by a tumor virus, the method including the step of administering, to a subject, an effective amount of a component that targets a gene product of the tumor virus.

The present disclosure, in one aspect, is capable of providing a pharmaceutical composition to a tumor in which a tumor virus is involved, or a method for treating the same.

DETAILED DESCRIPTION

Figure 1:
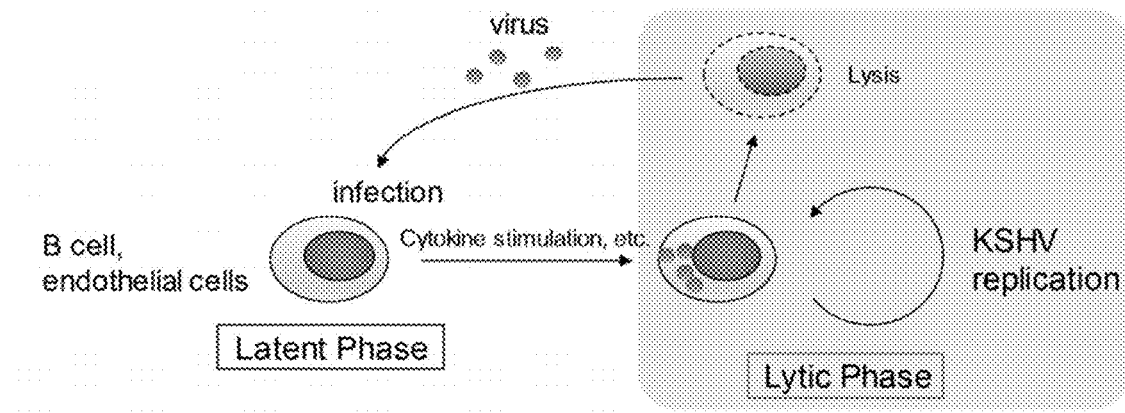
FIG. 1 is a schematic diagram that explains a life cycle of KSHV.

The present disclosure, in one aspect, is based on the finding that the growth of viral tumors can be significantly suppressed by suppressing the expression of a virus gene product.

The common method for treating a malignant tumor is, for example, surgery, pharmacotherapy, radiotherapy, or combinations of these.

The pharmacotherapy is, for example, chemotherapy (anti-cancer therapy), hormonotherapy (endocrine therapy), molecularly targeted therapy, or differentiation therapy.

Generally, even in a case of a viral tumor, when the tumor is formed, an anticancer agent or a molecular target drug targets the tumor cells and/or a protein in the tumor cells.

In contrast, the present disclosure, in one aspect, is based on the finding that in a tumor in which a tumor virus is involved, the growth of the tumor can be suppressed by suppressing the expression of a virus gene product.

In other words, the present disclosure, in one aspect, relates to a pharmaceutical composition for preventing, ameliorating, suppressing the progression of, and/or treating, a tumor caused by a tumor virus, the pharmaceutical composition containing a component that targets a gene product of the tumor virus as an active ingredient.

[Active Ingredient]

The pharmaceutical composition according to the present disclosure contains a component that targets a gene product of a tumor virus, as an active ingredient.

In the present disclosure, the "component that targets a gene product of a tumor virus" is a component that suppresses the expression and/or function of a gene product of a tumor virus, in one or a plurality of embodiments. In one or a plurality of embodiments, the component is a component that suppresses the transcription and/or translation of a gene of a genome of a tumor virus.

Alternatively, the "component that targets a gene product of a tumor virus" is a component that suppresses an increase in the tumor virus copy number, in one or a plurality of embodiments.

[Targeted Gene Product]

The gene product targeted by the "component that targets a gene product of a tumor virus" is a product of a gene that is involved in a life cycle of the tumor virus, in one or a plurality of embodiments.

In one or a plurality of embodiments, the "gene that is involved in a life cycle" is a gene that encodes a protein that is involved in switching from latent infection to lytic infection of a tumor virus; and/or a gene whose expression is induced or accelerated in the lytic phase of a tumor virus.

Therefore, the gene product targeted by the "component that targets a gene product of a tumor virus," in one or a plurality of embodiments, is a gene whose expression is induced or accelerated at the start of lytic infection of a tumor virus, or a gene whose expression is induced or accelerated during a period of lytic infection of a tumor virus.

As a non-limiting example, in a case of Kaposi sarcoma-associated herpesvirus (KSHV), an example of the gene product whose expression is induced or accelerated at the start of lytic infection is RTA (also referred to as ORF50). RTA is a lytic switch protein of KSHV.

Besides, the gene product whose expression is induced or accelerated in the lytic phase of KSHV is, for example, ORF57, K-bZIP, ORF59, vIL-6, or the like.

[Tumor Caused by Tumor Virus]

In the present disclosure, a tumor as a subject of treatment and the like is a tumor caused by a tumor virus, which is a malignant tumor, in one or a plurality of embodiments.

To a malignant tumor that is generally difficult to treat, the pharmaceutical composition according to the present disclosure can provide a novel therapy or other means.

In one or a plurality of embodiments, the "tumor caused by a tumor virus" refers to a tumor formed by involvement of a tumor virus, a tumor in which a virus is detected, and such a tumor that the tumor formation is caused by a virus.

In one or a plurality of embodiments, the "tumor virus" refers to a virus involved in tumor formation, or a virus that is a cause of tumor formation.

In one or a plurality of embodiments, examples of the "tumor caused by a tumor virus" include a virus-associated tumor, examples of which include hepatocellular carcinoma, cervical epithelial dysplasia, cervical cancer, oropharyngeal cancer, adult T cell leukemia, malignant lymphoma, Merkel cell carcinoma, primary effusion lymphoma, and Kaposi sarcoma.

In one or a plurality of embodiments, examples of the "tumor virus" include EB virus (EBV), hepatitis B virus (HBV), hepatitis C virus (HCV), human papillomavirus (HPV), human T-lymphotropic/leukemia virus types I (HTLV-1), Kaposi sarcoma-associated herpesvirus (KSHV), and Merkel cell polyomavirus (MCV).

In one or a plurality of embodiments, the "component that targets a gene product of a tumor virus" in the pharmaceutical composition according to the present disclosure is, a low-molecular-weight compound.

In one or a plurality of embodiments, the low-molecular-weight compound that targets a gene product of a tumor virus, the low-molecular-weight compound that suppresses the transcription and/or translation of a gene of a genome of a tumor virus, or the low-molecular-weight compound that suppresses the transcription and/or translation of a gene of a genome of a DNA tumor virus is a compound expressed by the following formula (I), or a pharmaceutically acceptable salt of the compound:

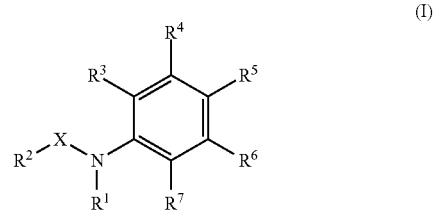

(I)

where $R^1$ represents a hydrogen atom; a substituted or unsubstituted $C_{1-6}$ alkyl group; a substituted or unsubstituted $C_{2-6}$ alkenyl group; a substituted or unsubstituted $C_{2-6}$ alkynyl group; or a substituted or unsubstituted 5 to 8 membered aryl group, X represents —C(=O)—; —C(=S)—; —SO$_2$—; —C(=S)NHC(=O)—; or —C(=O)NHC(=S)—, $R^2$ represents a substituted or unsubstituted $C_{1-6}$ alkyl group; a substituted or unsubstituted $C_{2-6}$ alkenyl group; a substituted or unsubstituted $C_{2-6}$ alkynyl group; a substituted or unsubstituted 5 to 8 membered aryl group; a substituted or unsubstituted nitrogen-containing hetero ring; or substituted or unsubstituted fused heteroaryl group, $R^3$ represents a hydrogen atom; a substituted or unsubstituted $C_{1-6}$ alkyl group; a $C_{2-6}$ alkenyl group; a $C_{2-6}$ alkynyl group; a halogen atom; —CN; —NH$_2$; or —NO$_2$, $R^4$ represents a hydrogen atom; a halogen atom; a substituted or unsubstituted $C_{1-6}$ alkyl group; a substituted or unsubstituted $C_{2-6}$ alkenyl group; a substituted or unsubstituted $C_{2-6}$ alkynyl group; or a substituted or unsubstituted $C_{6-10}$ aryl group, $R^5$ represents a hydrogen atom; a halogen atom; an amino group; or an azide group, $R^6$ represents a hydrogen atom; —CSO$_2$NR$^{10}$R$^{11}$—, or —CSO$_2$R$^{12}$, where $R^{10}$, $R^{11}$, and $R^{12}$ independently represent a hydrogen atom; a substituted or unsubstituted $C_{1-6}$ alkyl group; a substituted or unsubstituted $C_{2-6}$ alkenyl group; a substituted or unsubstituted $C_{2-6}$ alkynyl group; a substituted or unsubstituted $C_{1-4}$ alkoxy $C_{1-4}$ alkyl group; a substituted or unsubstituted cycloalkyl group; a substituted or unsubstituted heterocycloalkyl group; a substituted or unsubstituted aromatic ring; or a substituted or unsubstituted heteroaryl group, $R^{10}$ and $R^{11}$ each form a heterocycloalkyl group in combination with a nitrogen atom to which the same is bonded, or $R^{10}$ and $R^{11}$ each form a heterocycloalkyl group in combination with a nitrogen atom to which the same is bonded and a sulfur atom coupled with the nitrogen atom, and $R^7$ represents a hydrogen atom; a halogen atom; a diethylamino group; a substituted or unsubstituted nitrogen-containing heterocycloalkyl group; or a substituted or unsubstituted nitrogen-containing heteroaryl group.

The "$C_{1-6}$ alkyl group" in the present disclosure means a linear or branched chain alkyl group having one to six carbon atoms, which is a monovalent group derived from an aliphatic hydrocarbon having one to six carbon atoms by removing one arbitrary hydrogen atom therefrom. In one or a plurality of embodiments, the $C_{1-6}$ alkyl group is a methyl group, an ethyl group, a 1-propyl group, a 2-propyl group, a 2-methyl-1-propyl group, a 2-methyl-2-propyl group, an n-butyl group, an isobutyl group, a tert-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, or a 2,3-dimethyl-2-butyl group.

The "$C_{2-6}$ alkenyl group" in the present disclosure means a linear or branched chain alkenyl group having two to six carbon atoms. In one or a plurality of embodiments, the $C_{2-6}$ alkenyl group is a vinyl group, an allyl group, a 1-propenyl group, a 2-propenyl group, a 1-butenyl group, a 2-butenyl group, a 3-butenyl group, a pentenyl group, or a hexenyl group.

The "$C_{2-6}$ alkynyl group" in the present disclosure means a linear or branched chain alkynyl group having two to six carbon atoms. In one or a plurality of embodiments, the $C_{2-6}$ alkynyl group is an ethynyl group, a 1-propynyl group, a 2-propynyl group, a butynyl group, a pentynyl group, or a hexynyl group.

The "$C_{1-6}$ alkoxy group" in the present disclosure means an oxy group to which a $C_{1-6}$ alkyl group is bonded. In one or a plurality of embodiments, the $C_{1-6}$ alkoxyl group is a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, or a 2,3-dimethyl-2-butyloxy group.

The "$C_{1-4}$ alkoxycarbonyl group" in the present disclosure means a carbonyl group to which a $C_{1-4}$ alkoxy group is bonded. In one or a plurality of embodiments, the $C_{1-4}$ alkoxycarbonyl group is a methoxycarbonyl group, an ethoxycarbonyl group, a 1-propyloxycarbonyl group, or a 2 propyloxycarbonyl group.

The "$C_{1-4}$ alkoxy $C_{1-4}$ alkyl group" in the present disclosure means a $C_{1-4}$ alkyl group to which a $C_{1-4}$ alkoxy group is bonded. In one or a plurality of embodiments, the $C_{1-4}$ alkoxycarbonyl group is a methoxyethyl group, or an ethoxymethyl group.

The "cycloalkyl group" in the present disclosure means an alicyclic hydrocarbon group. In one or a plurality of embodiments, the cycloalkyl group is a 3 to 7 membered cycloalkyl group. In one or a plurality of embodiments, the cycloalkyl group may have a single-ring structure, or a double-ring structure. In one or a plurality of embodiments, the cycloalkyl group is a cyclopropyl group, a cyclobutyl group, a cyclopentyl group, or a cyclohexyl group.

The "heterocycloalkyl group" in the present disclosure means a cycloalkyl group in which one or two carbon atoms constituting a ring are substituted with heteroatoms, such as nitrogen atoms, oxygen atoms, or sulfur atoms. In one or a plurality of embodiments, the heterocycloalkyl group is a 3 to 7 membered heterocycloalkyl group. In one or a plurality of embodiments, the heterocycloalkyl group may have a single-ring structure, or a double-ring structure. In one or a plurality of embodiments, the heterocycloalkyl group is an aziridinyl group, an azetidinyl group, a pyrrolidinyl group, a tetrahydrofuranyl group, a tetrahydrothiophenyl group, a piperidinyl group, a piperadizinyl group, a piperazinyl group, a tetrahydropyranyl group, a tetrahydro-thio-pyranyl group, or a morpholinyl group.

The "aryl group" in the present disclosure means an aromatic hydrocarbon cyclic group. In one or a plurality of embodiments, the aryl group is a 5 to 12 membered aryl group. The aryl group may have a single-ring structure, or a double-ring structure. In one or a plurality of embodiments, the aryl group is a phenyl group, a 1-naphthyl group, or a 2-naphthyl group.

The "heteroaryl group" in the present disclosure means an aryl group in which one or two carbon atoms constituting a ring are substituted with heteroatoms, such as nitrogen atoms, oxygen atoms, or sulfur atoms. In one or a plurality of embodiments, the heteroaryl group is a 5 to 12 membered heteroaryl group. The aryl group may have a single-ring structure, or a double-ring structure. In one or a plurality of embodiments, the heteroaryl group is a furanyl group, a thiophenyl group, a pyrrolyl group, an imidazolyl group, a pyrazolyl group, a triazolyl group, a tetrazolyl group, a thiazolyl group, an oxazolyl group, an isoxazolyl group, an oxadiazolyl group, an oxo-pyridyl group, a thiadiazolyl group, an isothiazolyl group, a pyridyl group, a pyridazyl group, a pyradinyl group, a pyrimidyl group, a quinazolinyl group, a quinolinyl group, an isoquinolinyl group, a benzoimidazoyl group, a benzofuranyl group, a benzothiophenyl group, an indolyl group, or an indazolyl group.

The "nitrogen-containing heteroaryl group" in the present disclosure means a heteroaryl group in which one or two carbon atoms constituting a ring are substituted with nitrogen atoms. In one or a plurality of embodiments, the nitrogen-containing heteroaryl group is a pyridyl group, a pyrrolyl group, an oxazoyl group, an isoxazolyl group, a thiazolyl group, an isothiazolyl group, an indolyl group, an isoindolyl group, a triazoyl group, a pyrazoyl group, a pyridazoyl group, a pyrimidyl group, a pyradinyl group, a quinolinyl group, an isoquinolinyl group, or a benzoimidazoyl group.

The phrase of "substituted or unsubstituted" in the present disclosure means that there is one or a plurality of substituent groups in an arbitrary combination at substitutable sites, or there is no substituent group. The substituent group is, for example, a halogen atom, a cyano group, a trifluoro methyl group, a nitro group, a hydroxyl group, a mercapto group, a formyl group, an oxo group, an imino group, a methylenedioxy group, a C$_{1-6}$ alkyl group, a C$_{1-6}$ alkoxy group, a benzyloxy group, a C$_{1-6}$ alkanoyloxy group, an amino group, a mono C$_{1-6}$ alkylamino group, a di-C$_{1-6}$ alkylamino group, a carbamoyl group, a C$_{1-6}$ alkylaminocarbonyl group, di-C$_{1-6}$ alkylaminocarbonyl group, a carboxyl group, a C$_{1-6}$ alkoxycarbonyl group, a C$_{1-6}$ alkylthio group, a C$_{1-6}$ alkylsulfinyl group, a C$_{1-6}$ alkylsulfonyl group, a C$_{1-6}$ alkanolyamino group, or a C$_{1-6}$ alkylsulfonamide group. In one or a plurality of embodiments, the halogen atom is fluorine, chlorine, bromine, or iodine.

The "C$_{1-6}$ alkyl group that may have a halogen atom in the substituent group" in the present disclosure means a C$_{1-6}$ alkyl group in which at least an arbitrary carbon atom is substituted with a halogen atom. In one or a plurality of embodiments, examples of the C$_{1-6}$ alkyl group that may have a halogen atom in the substituent group include a trifluoromethyl group, a difluoromethyl group, and a monofluoromethyl group.

In one or a plurality of embodiments, the compound expressed by Formula (I) is a compound expressed by Formula (II):

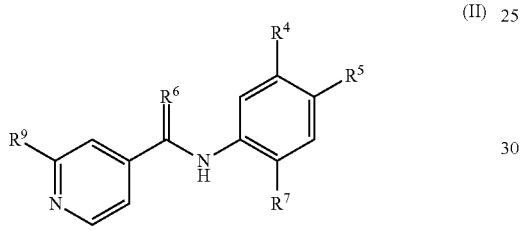

(II)

where
R$^4$ represents a hydrogen atom; a halogen atom; a substituted or unsubstituted C$_{1-6}$ alkyl group; a substituted or unsubstituted C$_{2-6}$ alkenyl group; a substituted or unsubstituted C$_{2-6}$ alkynyl group; or a substituted or unsubstituted aryl group,
R$^5$ represents a hydrogen atom; a halogen atom; an amino group; or an azide group,
R$^7$ represents a hydrogen atom; a halogen atom; a diethylamino group; a substituted or unsubstituted nitrogen-containing heterocycloalkyl group; or a substituted or unsubstituted nitrogen-containing heteroaryl group,
R$^8$ represents an oxygen atom or a sulfur atom, and
R$^9$ represents a hydrogen atom; a C$_{1-6}$ alkyl group; or a C$_{2-6}$ alkynyl group.

In one or a plurality of embodiments, R$^4$ represents a hydrogen atom, a halogen atom, or a C$_{1-6}$ alkyl group having a substitution with a halogen atom, and preferably represents a hydrogen atom, a fluorine atom, or a trifluoromethyl group.

In one or a plurality of embodiments, R$^5$ represents a hydrogen atom, an amino group, or an azide group, and preferably represents a hydrogen atom.

In one or a plurality of embodiments, R$^7$ represents a substituted or unsubstituted nitrogen-containing heterocycloalkyl group, or a substituted or unsubstituted nitrogen-containing heteroaryl group; preferably represents a substituted or unsubstituted nitrogen-containing heterocycloalkyl group; and more preferably represents a substituted or unsubstituted piperidinyl group. In one or a plurality of embodiments, examples of R$^7$ include the following groups. In the following groups, a bonding hand to which wavy lines are attached is a bonding part where the group is bonded with the compound expressed by Formula (II):

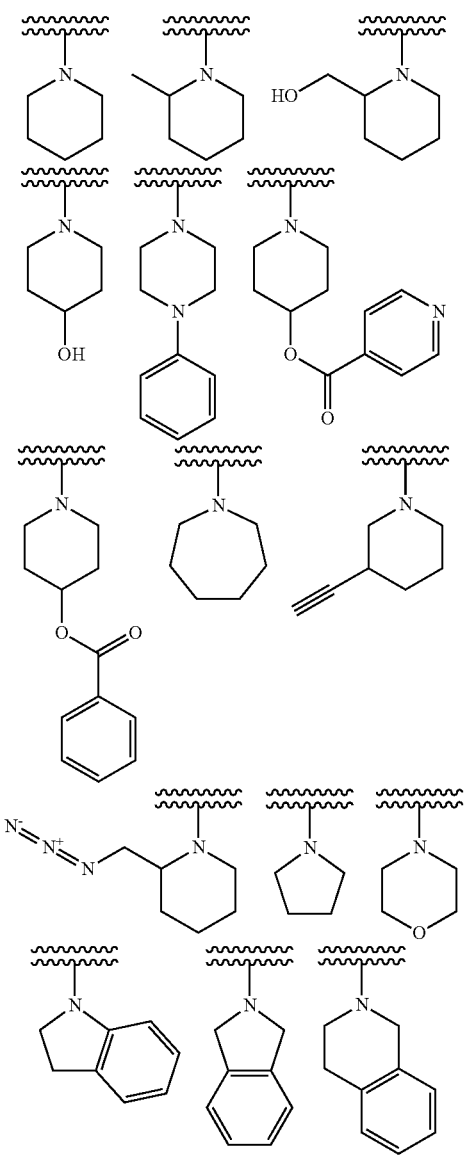

In one or a plurality of embodiments, R$^9$ represents a hydrogen atom or an ethynyl group, and preferably represents a hydrogen atom.

In one or a plurality of embodiments, examples of the compound expressed by Formula (II) include compounds expressed by the following formulae:

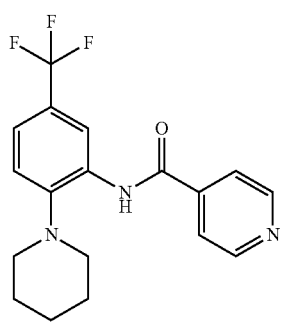

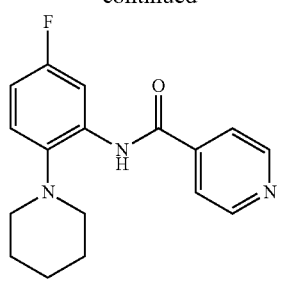
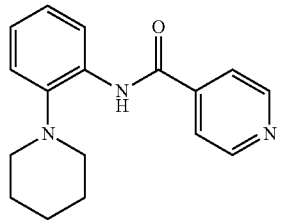
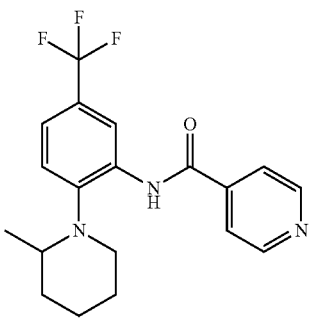
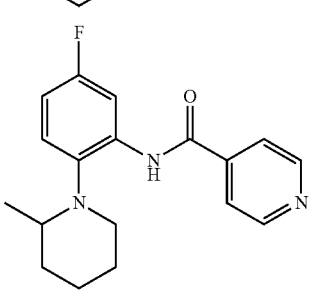
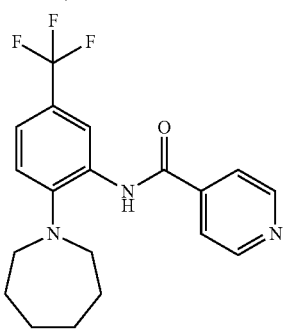
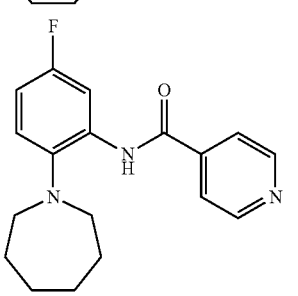
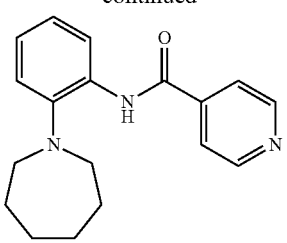
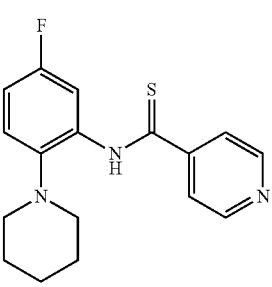
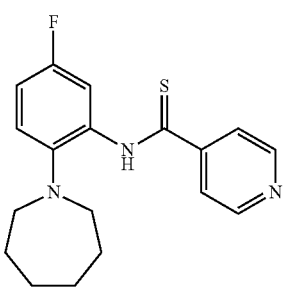
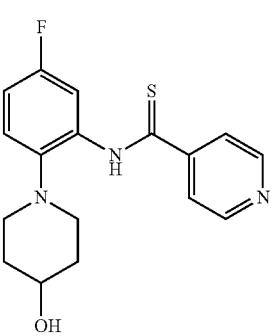
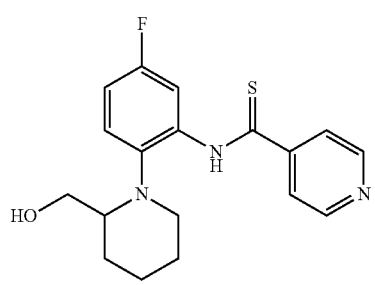

-continued
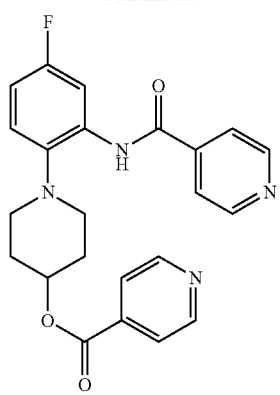
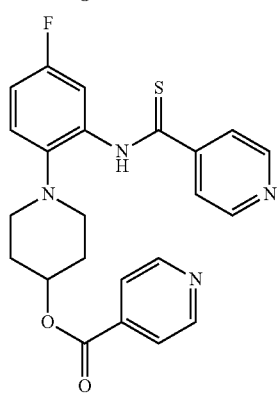
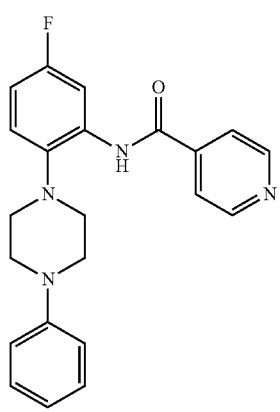
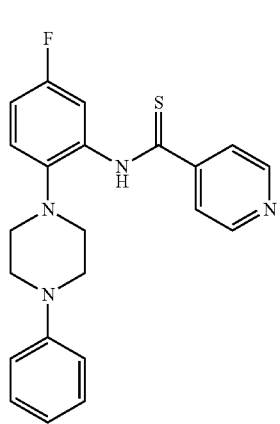
-continued
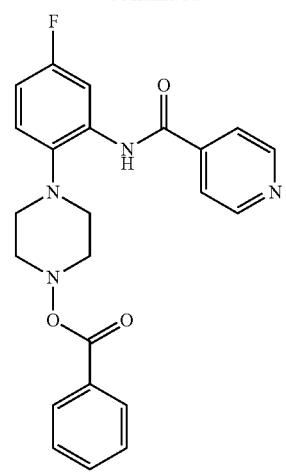
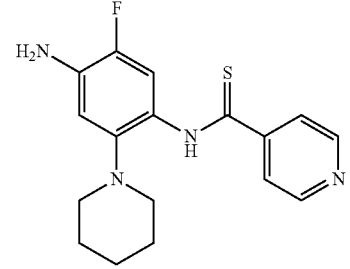
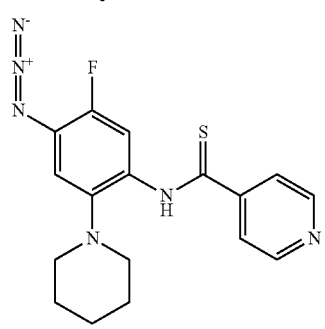
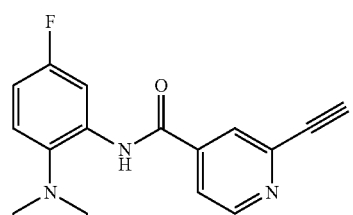
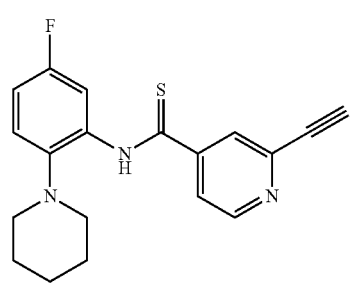

-continued

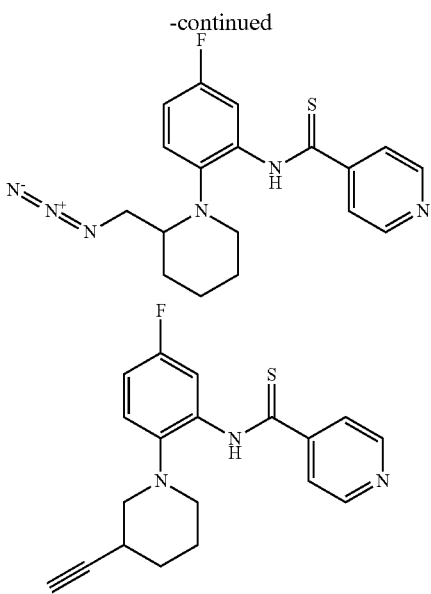

In one or a plurality of embodiments, among these, N-[5-fluoro-2-(1-piperidinyl)phenyl]-4-pyridinethioamide expressed by the following formula is preferred as the compound expressed by Formula (I):

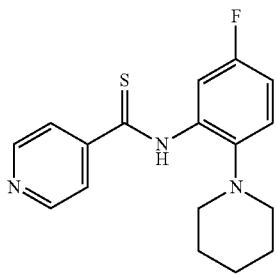

In one or a plurality of embodiments, the compounds expressed by Formula (I) in the present disclosure or salts of the same can be produced with reference to a known producing method or WO2009/020198.

In the present disclosure, the "pharmaceutically acceptable salt" means a pharmacologically and/or pharmaceutically acceptable salt. It is, for example, an inorganic acid salt, an organic acid salt, an inorganic base salt, an organic base salt, an acidic amino acid salt, or a basic amino acid salt. In one or a plurality of embodiments, the inorganic acid salt is a hydrochloride, a hydrobromate, a sulfate, a nitrate, or a phosphate. In one or a plurality of embodiments, the organic acid salt is an acetate, a succinate, a fumarate, a maleate, a tartrate, a citrate, a lactate, a stearate, a benzoate, a methanesulfonate, or a p-toluenesulfonate. In one or a plurality of embodiments, the inorganic base salt is a salt of an alkali metal such as a sodium salt or a potassium salt, an alkali earth metal salt such as a magnesium salt or a calcium salt, an aluminum salt, or an ammonium salt. In one or a plurality of embodiments, the organic base salt is a diethylamine salt, a diethanolamine salt, a meglumine salt, or an N,N'-dibenzylethylenediamine salt. In one or a plurality of embodiments, the acidic amino acid salt is an aspartate, or a glutamate. In one or a plurality of embodiments, the basic amino acid salt is an arginine salt, a lysine salt, or an ornithine salt.

In the present disclosure, the "salt of a compound" may encompass a hydrate that can be formed when a compound, left in the atmosphere, absorbs moisture. Further, in the present disclosure, the "salt of a compound" may also encompass a solvate that can be formed when a compound absorbs a solvent of another kind.

The above-described compounds, which are active ingredients of pharmaceutical compositions according to the present disclosure, may be contained in the pharmaceutical composition, in the form of prodrugs. In one or a plurality of embodiments, the "prodrug" may be a compound that is easily hydrolyzed in a living organism to regenerate the above-described compound; in a case of a compound having a carboxyl group, the prodrug of the compound may be a compound in which the carboxyl group is converted to an alkoxycarbonyl group; a compound in which the carboxyl group is converted to an alkylthiocarbonyl group; or a compound in which the carboxyl group is converted to an alkylaminocarbonyl group. Alternatively, in a case of a compound having, for example, an amino group, the prodrug of the compound is, for example, a compound in which the amino group is substituted with an alkanoyl group to form an alkanoylamino group; a compound in which the amino group is substituted with an alkoxycarbonyl group to form an alkoxycarbonylamino group; a compound in which the amino group is converted to an acyloxymethylamino group; or a compound in which the amino group is converted to hydroxylamine. Further alternatively, in a case of a compound having, for example, a hydroxyl group, the prodrug of the compound is, for example, a compound in which the hydroxyl group is substituted with the acyl group to form an acyloxy group; a compound in which the hydroxyl group is converted to a phosphoric ester; or a compound in which the hydroxyl group is converted to an acyloxymethyloxy group. The alkyl part of the group used for the conversion to these prodrugs is, for example, an alkyl group, as will be described later, and the alkyl group may be substituted (for example, with an alkoxy group having one to six carbon atoms). In one or a plurality of embodiments when the prodrug is a compound obtained by converting the carboxyl group to an alkoxycarbonyl group, the compound is, for example, a lower alkoxycarbonyl (e.g., having one to six carbon atoms) such as methoxycarbonyl or ethoxycarbonyl, or a lower alkoxycarbonyl (e.g., having one to six carbon atoms), in which the carboxyl group is substituted with an alkoxy group, such as methoxymethoxycarbonyl, ethoxymethoxycarbonyl, 2-methoxyethoxycarbonyl, 2-methoxyethoxymethoxycarbonyl, or pivaloyloxymethoxycarbonyl.

In one or a plurality of embodiments, the "pharmaceutical composition" in the present disclosure may have a dosage form suitable for an administration form by using the known formulation technology. The pharmaceutical composition can be administered, for example, orally in such a dosage form (though not limited to) as tablets, capsules, granules, powder, pills, troche, syrups, and liquid formulations. Alternatively, the pharmaceutical composition can be administered parenterally in such a dosage form (though not limited to) as injection, liquid formulations, aerosols, suppositories, patches, cataplasm, lotions, liniments, ointments, and eye drops. These formulations can be produced by a known method using additives (but not limited to) such as excipients, lubricants, binders, disintegrators, stabilizers, corrigents, and diluents.

The excipient is, for example (though not limited to), a starch such as starch, potato starch, or corn starch; lactose; crystalline cellulose; or calcium hydrogen phosphate. The lubricant is, for example (though not limited to), ethyl cellulose; hydroxypropyl cellulose; hydroxypropyl methylcellulose; shellac; talc; carnauba wax; or paraffin. Examples of the binder include (though not limited to) the following: polyvinyl pyrrolidone; macrogol; and the compounds similar to those given as examples of the excipient. Examples of the disintegrator include (though not limited to) the following: compounds similar to those given as examples of the excipient; and chemically modified starches and celluloses such as croscarmellose sodium, sodium carboxymethyl starch, and cross-linked polyvinyl pyrrolidone. Examples of the stabilizer include (though not limited to) the following: paraoxybenzoic acid esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid. The corrigent is, for example (though not limited to), a commonly used sweetener, an acidulant, or a flavor.

The preparation of a liquid formulation may use (but not limited to) ethanol, phenol, chlorocresol, purified water, or distilled water as a solvent, and may also use a surface-active agent or an emulsifying agent as required. The surface-active agent or the emulsifying agent is, for example (though not limited to), polysorbate 80, polyoxyl 40 stearate, or lauromacrogol.

The method for using the pharmaceutical composition of the present disclosure may differ depending on symptoms, ages, administration methods, etc. Regarding how to use the composition, in a case where the active ingredient is the above-described low-molecular-weight compound, the pharmaceutical composition can be intermittently or continuously administered, for example (though not limited to), orally, percutaneously, submucosally, subcutaneously, intramuscularly, intravascularly, intracerebrally, or intraperitoneally so that the concentration thereof is in the range of 100 nM to 1 mM. In a non-limiting embodiment, for oral administration the pharmaceutical composition may be administered to a subject (e.g., an adult human if the subject is a human) based on the symptom, in a daily dosage of from 0.01 mg (preferably 0.1 mg) as a lower limit to 2000 mg (preferably 500 mg and more preferably 100 mg) as a higher limit, which is expressed in terms of the low-molecular-weight compound expressed as Formula (I) described above, at once or in batches. In a non-limiting embodiment, for intravenous administration the pharmaceutical composition may be administered to a subject (e.g., an adult human if the subject is a human) based on the symptom, in a daily dosage of from 0.001 mg (preferably 0.01 mg) as a lower limit to 500 mg (preferably 50 mg) as a higher limit, at once or in batches.

The method for using the pharmaceutical composition of the present disclosure may be used in combination with another medicine.

[Method for Preventing, Ameliorating, Suppressing Progression of, and/or Treating Tumors Caused by Tumor Viruses]

The present disclosure, in one aspect, relates to a method for preventing, ameliorating, suppressing the progression of, and/or treating, a tumor caused by a tumor virus, the method including the step of administering, to a subject, an effective amount of a component that targets a gene product of the tumor virus.

In one or a plurality of embodiments, the present aspect includes administering an effective amount of the pharmaceutical composition to a subject.

In one or a plurality of embodiments, the prevention, amelioration, suppression of progression, and/or treatment, of a tumor caused by a tumor virus may encompass suppressing formation of the tumor, suppressing growth of the tumor, and suppressing augmentation of the tumor.

In one or a plurality of embodiments, the administration of the pharmaceutical composition according to the present disclosure may conform to the above-described method for using the pharmaceutical composition.

The subject is, for example, a subject (patient) from which a tumor caused by a tumor virus is detected.

Further, the subject is, for example, a human, or an animal other than humans.

In the present aspect, a tumor virus, a tumor, active ingredients, a pharmaceutical composition, a method for using the same, and the like, may be set as described above.

The present disclosure, in another aspect, relates to use of a component that targets a gene product of a tumor virus, for preventing, ameliorating, suppressing the progression of, and/or treating, a tumor caused by the tumor virus.

The present disclosure, in another one or more embodiments, relates to use of a component that targets a gene product of a tumor virus, for producing a pharmaceutical composition for preventing, ameliorating, suppressing the progression of, and/or treating, a tumor caused by the tumor virus.

The present disclosure may relate to one or a plurality of embodiments described below:

[1] A pharmaceutical composition for preventing, ameliorating, suppressing the progression of, and/or treating, a tumor caused by a tumor virus, the pharmaceutical composition containing a component that targets a gene product of the tumor virus as an active ingredient.

[2] The pharmaceutical composition according to [1], wherein the component that targets a gene product of a tumor virus is a component that suppresses the expression and/or function of the gene product of the tumor virus.

[3] The pharmaceutical composition according to [1] or [2], wherein the gene product is a gene product that is involved in a life cycle of the tumor virus.

[4] The pharmaceutical composition according to any one of [1] to [3], wherein the gene product is a gene product whose expression is induced or accelerated at the start of, or during a period of, lytic infection of the tumor virus.

[5] The pharmaceutical composition according to [1], wherein the component that targets the gene product of the tumor virus is a component that suppresses an increase in the tumor virus copy number.

[6] The pharmaceutical composition according to any one of [1] to [5], wherein the component that targets the gene product of the tumor virus is a compound expressed by the following formula (I), or a pharmaceutically acceptable salt of the compound:

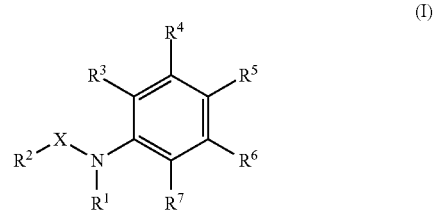

where
R¹ represents a hydrogen atom; a substituted or unsubstituted $C_{1-6}$ alkyl group; a substituted or unsubstituted $C_{2-6}$ alkenyl group; a substituted or unsubstituted $C_{2-6}$ alkynyl group; or a substituted or unsubstituted aryl group, X represents —C(=O)—; —C(=S)—; —SO₂—; —C(=S)NHC(=O)—; or —C(=O)NHC(=S)—, R² represents a substituted or unsubstituted $C_{1-6}$ alkyl group; a substituted or unsubstituted $C_{2-6}$ alkenyl group; a substituted or unsubstituted $C_{2-6}$ alkynyl group; a substituted or unsubstituted aryl group; a substituted or unsubstituted nitrogen-containing heteroaryl group, R³ represents a hydrogen atom; a substituted or unsubstituted $C_{1-6}$ alkyl group; a $C_{2-6}$ alkenyl group; a $C_{2-6}$ alkynyl group; a halogen atom; —CN; —NH₂; or —NO₂, R⁴ represents a hydrogen atom; a halogen atom; a substituted or unsubstituted $C_{1-6}$ alkyl group; a substituted or unsubstituted $C_{2-6}$ alkenyl group; a substituted or unsubstituted $C_{2-6}$ alkynyl group; or a substituted or unsubstituted aryl group, R⁵ represents a hydrogen atom; a halogen atom; an amino group; or an azide group, R⁶ represents a hydrogen atom; —CSO₂NR¹⁰R¹¹—, or —CSO₂R¹²,
where R¹⁰, R¹¹, and R¹² independently represent a hydrogen atom; a substituted or unsubstituted $C_{1-6}$ alkyl group; a substituted or unsubstituted $C_{2-6}$ alkenyl group; a substituted or unsubstituted $C_{2-6}$ alkynyl group; a substituted or unsubstituted $C_{1-4}$ alkoxy $C_{1-4}$ alkyl group; a substituted or unsubstituted cycloalkyl group; a substituted or unsubstituted heterocycloalkyl group; a substituted or unsubstituted aromatic ring; or a substituted or unsubstituted heteroaryl group, R¹⁰ and R¹¹ each form a heterocycloalkyl group in combination with a nitrogen atom to which the same is bonded, or R¹⁰ and R¹¹ each form a heterocycloalkyl group in combination with a nitrogen atom to which the same is bonded and a sulfur atom coupled with the nitrogen atom, and R⁷ represents a hydrogen atom; a halogen atom; a diethylamino group; a substituted or unsubstituted nitrogen-containing heterocycloalkyl group; or a substituted or unsubstituted nitrogen-containing heteroaryl group.

[7] The pharmaceutical composition according to any one of [1] to [5], wherein the component that targets the gene product of the tumor virus is a compound expressed by the following formula (II), or a pharmaceutically acceptable salt of the compound:

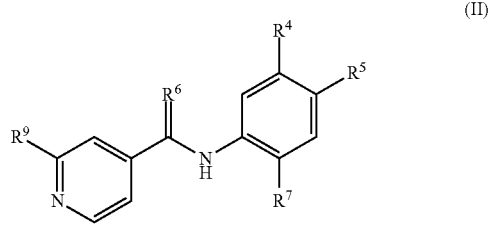

(II)

where
R⁴ represents a hydrogen atom; a halogen atom; a substituted or unsubstituted $C_{1-6}$ alkyl group; a substituted or unsubstituted $C_{2-6}$ alkenyl group; a substituted or unsubstituted $C_{2-6}$ alkynyl group; or a substituted or unsubstituted aryl group, R⁵ represents a hydrogen atom; a halogen atom; an amino group; or an azide group, R⁷ represents a hydrogen atom; a halogen atom; a diethylamino group; a substituted or unsubstituted nitrogen-containing heterocycloalkyl group; or a substituted or unsubstituted nitrogen-containing heteroaryl group, R⁸ represents an oxygen atom or a sulfur atom, and R⁹ represents a hydrogen atom; a $C_{1-6}$ alkyl group; or a $C_{2-6}$ alkynyl group.

[8] The pharmaceutical composition according to any one of [1] to [5], wherein the component that targets the gene product of the tumor virus is a compound expressed by the following formula, or a pharmaceutically acceptable salt of the compound:

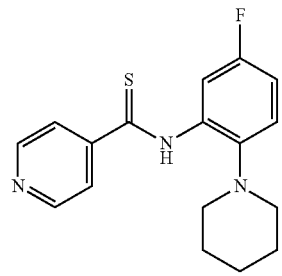 [SMILES: Fc1ccc(N2CCCCC2)c(NC(=S)c2ccncc2)c1]

[9] The pharmaceutical composition according to any one of [1] to [8], wherein the tumor is at least one selected from the group consisting of virus-associated tumors including hepatocellular carcinoma, cervical epithelial dysplasia, cervical cancer, oropharyngeal cancer, adult T cell leukemia, malignant lymphoma, Merkel cell carcinoma, primary effusion lymphoma, and Kaposi sarcoma.

[10] The pharmaceutical composition according to any one of [1] to [9], wherein the tumor virus is at least one selected from the group consisting of EB virus (EBV), hepatitis B virus (HBV), hepatitis C virus (HCV), human papillomavirus (HPV), human T-lymphotropic/leukemia virus types I (HTLV-1), Kaposi sarcoma-associated herpesvirus (KSHV), and Merkel cell polyomavirus (MCV).

[11] A method for preventing, ameliorating, suppressing the progression of, and/or treating, a tumor caused by a tumor virus, the method including the step of administering, to a subject, an effective amount of a component that targets a gene product of the tumor virus.

[12] The method according to [11], wherein the tumor caused by a tumor virus is a KSHV-associated tumor.

[13] The method according to [11], wherein the tumor caused by a tumor virus is a KSHV-induced lymphoma.

[14] The method according to [13], wherein the KSHV-induced lymphoma is a primary effusion lymphoma, a Kaposi sarcoma, or a multiple Castleman disease (MCD).

[15] The method according to any one of [11] to [14], the method including the step of administering, to a subject, an effective amount of the pharmaceutical composition according to any one of [1] to [10].

[16] Use of a component that targets a gene product of a tumor virus, in a method for preventing, ameliorating, suppressing the progression of, and/or treating, a tumor caused by the tumor virus, or production of a pharmaceutical composition for the same.

EXAMPLES

Hereinafter, although the following description describes the present disclosure in more detail by way of examples, these are illustrative, and the present disclosure is not limited to these examples. Note that all of the references cited in the present disclosure is incorporated as a portion of the present disclosure.

Production Example 1

Production of N-[5-fluoro-2-(1-piperidinyl)phenyl]-4-pyridinethioamide (Hereinafter Referred to as "Compound A" or "Cp. A")

A compound A expressed by the following chemical formula was produced with reference to Reference Example 11 of WO2009/020198:

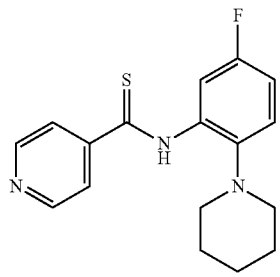 [SMILES: Fc1ccc(N2CCCCC2)c(NC(=S)c2ccncc2)c1]

Life Cycle of KSHV:

The life cycle of herpesviruses including KSHV is explained based on FIG. 1.

First, virus particles infect host cells, whereby a latent phase is established. Next, cytokine stimulation or the like causes a transition to a lytic phase.

During this lytic phase, the virus replicates repeatedly, and lyses the host eventually, whereby many virus particles are released.

Primary Effusion Lymphoma (PEL):

PEL is a lymphoma which is a kind of non-Hodgkin lymphoma and is originated from the chest cavity, the abdominal cavity, or the pericardium cavity. Massive ascites occurs as a clinical condition of PEL.

PEL is caused by HSKV, in a patient with a weakened immune system (e.g., an HIV-infected patient). PEL has very severe prognosis, and the survival period is said to be 4 to 10 months.

PEL often shows resistance to chemotherapy, and does not express the cell marker CD20; therefore, the anti-CD20 antibody, which is significantly effective against a B-cell lymphoma, is not effective.

Reference Example 1

Lytic Induction of KSHV+ PEL Cells and Expression of Lytic Genes

Both of the BC-3 cells and the BCBL-1 cells are cell lines of KSHV+ PEL cells. Regarding the BC-3 cells, it is known that TPA (12-O-tetradecanoylphorbol-13-acetate) and SB (sodium butyrate) cause cytokine stimulation, which results in the lytic induction. Further, regarding the BCBL-1 cells, it is known that VPA (valproic acid) causes cytokine stimulation, which results in the lytic induction.

Such cytokine stimulation was given to the BC-3 cells and the BCBL-1 cells, and the cells were cultured for 24 hours or 48 hours. Then, RNA of the same was collected, and was subjected to RT-PCR. Exemplary results thereof are shown in FIG. 2.

Figure 2:
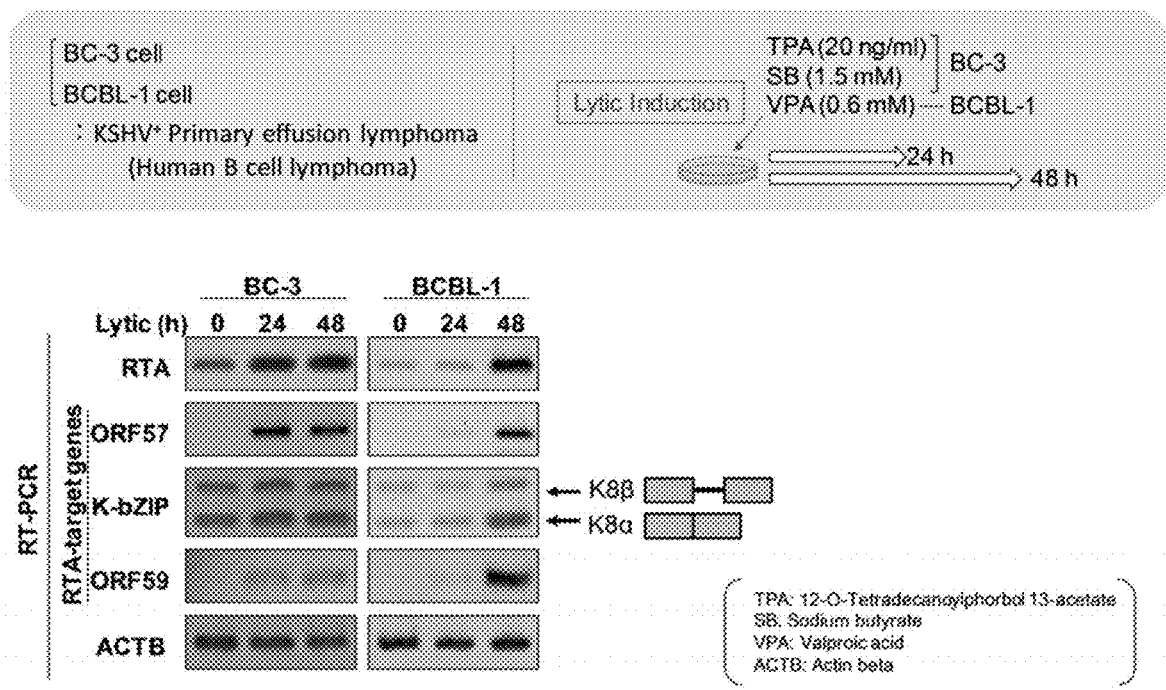
FIG. 2 illustrates an exemplary scheme for lytic induction with respect to KSHV$^+$ PEL cell lines (BC-3, BCBL-1), and results of the same (RT-PCR).

As illustrated in FIG. 2, acceleration of the expression of the RTA gene encoding a lytic switch protein, as well as three genes of ORF57, K8 (K-bZIP), and ORF59, which are lytic genes whose transcription are regulated by RTA, was confirmed, and lytic induction was confirmed.

Example 1

Suppression of Lytic Induction by Compound A

Effects of the compound A (the compound A produced in Production Example 1, also described as "Cp. A") were confirmed by using the same BC-3 cells and BCBL-1 cells as those in Reference Example 1.

The compound A was added to the BC-3 cells and the BCBL-1 cells undergoing lytic induction and cultured for 48 hours; then, the cultured cells were analyzed by RT-PCR and Western blotting. Exemplary results thereof are shown in FIG. 3.

Figure 3:
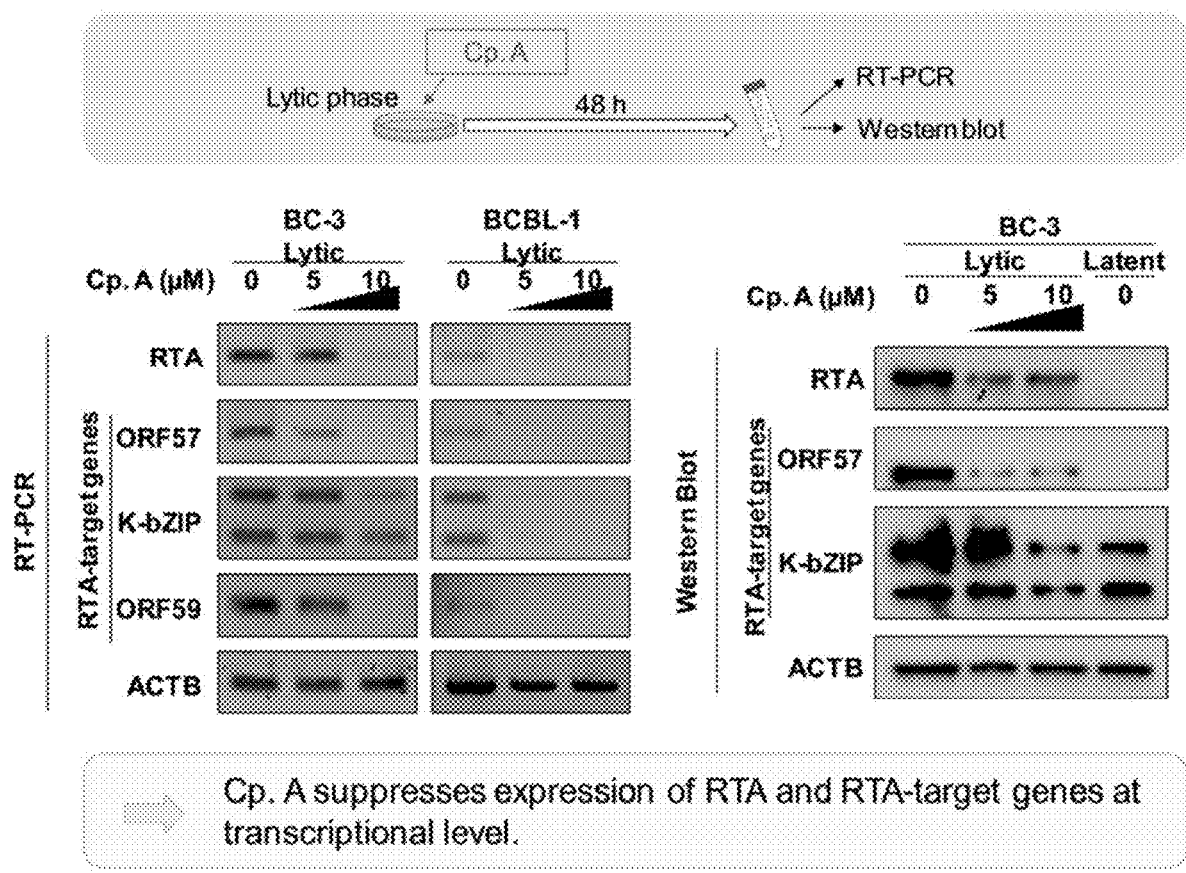
FIG. 3 illustrates an exemplary experiment scheme and results of the same (RT-PCR and Western blotting) indicating that a compound A (Cp. A) suppresses lytic genes on the transcription level.

It is recognized in the results of RT-PCR illustrated in FIG. 3 that the expression amount of lytic genes decreased as the added amount of the compound A increased to 5 μM, and to 10 μM.

Further, it is recognized in the results of Western blotting illustrated in FIG. 3 that the compound A suppressed expression of the lytic genes at protein level.

Example 2

Suppression of Viral Replication by Compound A

Effects of the compound A on the KSHV copy number were analyzed by real-time PCR.

The compound A was added to the BCBL-1 cells undergoing lytic induction and cultured for 96 hours; then, DNA samples were collected and analyzed by real-time PCR. Exemplary results thereof are shown in FIG. 4.

Figure 4:
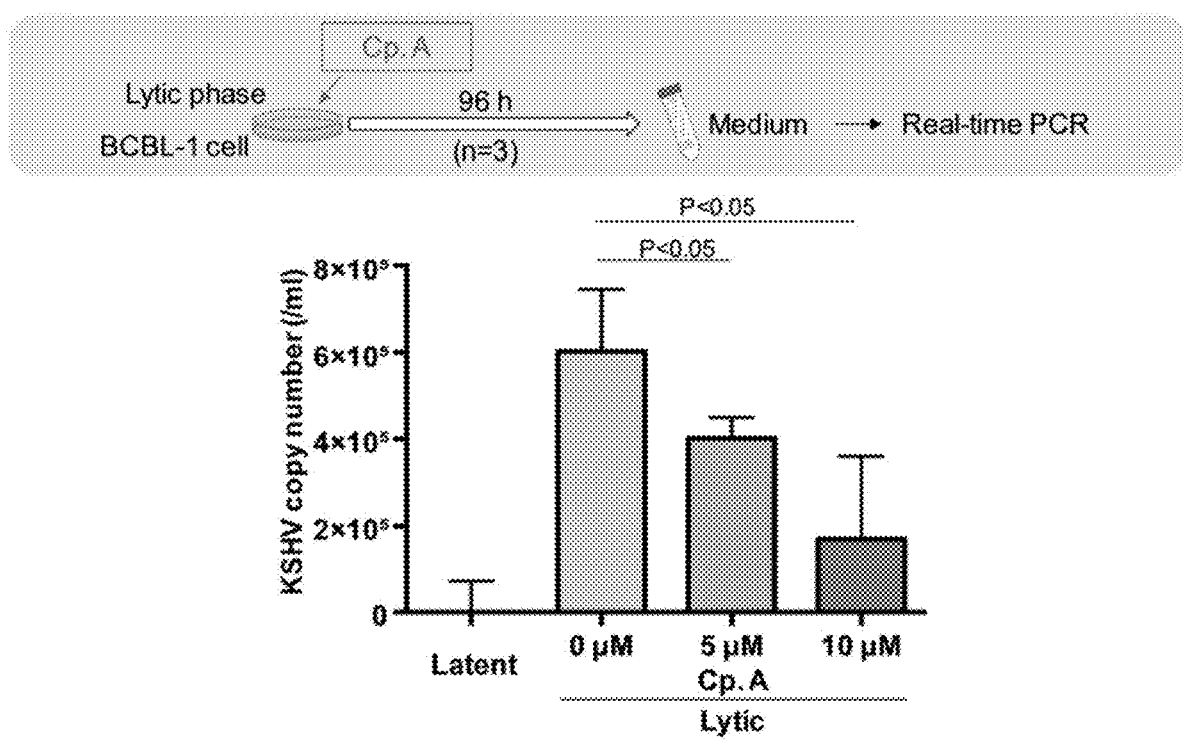
FIG. 4 illustrates an exemplary experiment scheme and results of the same (real-time PCR) indicating that the compound A (Cp. A) suppresses an increase in the virus copy number in lytic infection.

It is recognized that the virus copy number decreased as the added amount of the compound A increased to 5 μM, and to 10 μM, as illustrated in FIG. 4.

Example 3

Intraperitoneal Administration of Compound A to Xenograft Mouse Models

BCBL-1 cells were intraperitoneally inoculated into immunodeficient mice (NOD/SCID mice) so that PEL xenograft models were produced. PEL refers to "primary effusion lymphoma", as described above.

The mice were divided into a compound A administered group and a control group. The process was observed for 45 days, in which the compound A was administered intraperitoneally three times a week (300 mg/kg bw). To the control group, PBS was administered intraperitoneally three times a week instead of the compound A. Exemplary results thereof are shown in FIG. 5.

Figure 5:
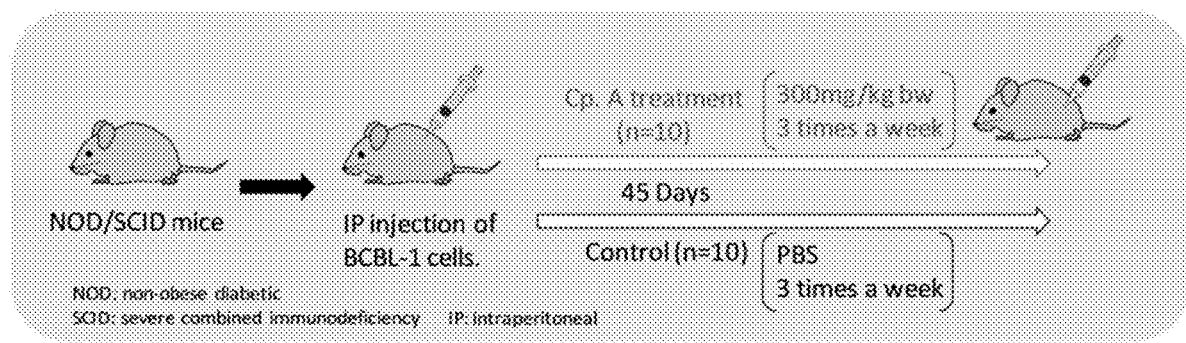
FIG. 5 illustrates an exemplary experiment scheme and results of the same (photographs of mice for comparison and a graph indicating the amount of ascites) for confirming the in-vivo tumor suppression effect of the compound A (Cp. A) in PEL xenograft mouse models.
Figure 5:
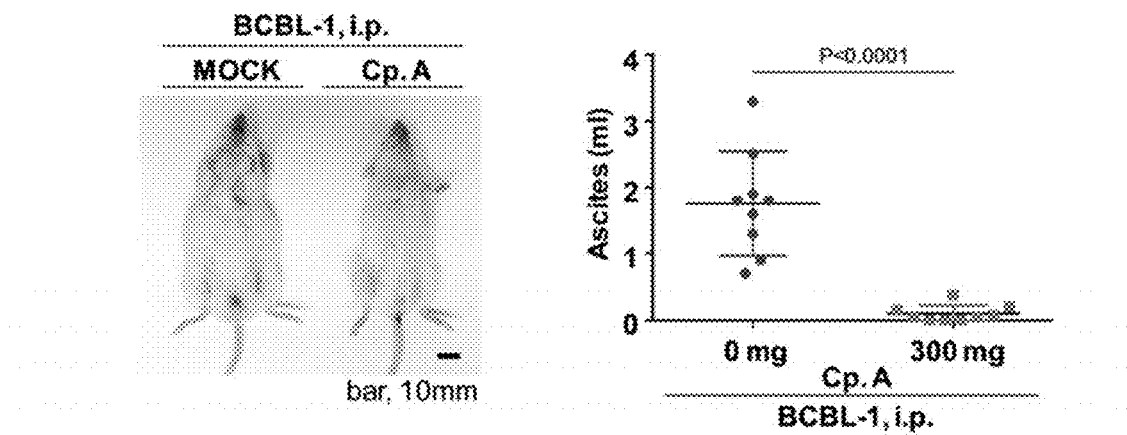

Photographs of mice shown in FIG. 5 show comparison between the mouse of the control group (MOCK) and the mouse of the compound A administered group. It was recognized that the abdomen of the mouse of the control group, to which the compound A was not administered, was significantly swollen with ascites.

The graph next to the photographs shows comparison of the amounts of ascites. The ascites of the mice of the compound A administered group was significantly less than that of the control group.

Further, hepatomegalia and enlarged spleen, which were secondarily caused by a lymphoma, were recognized in the mice of the control group, whereas enlarged spleen was particularly suppressed in the mice of the compound A administered group (data not shown).

Figure 6:
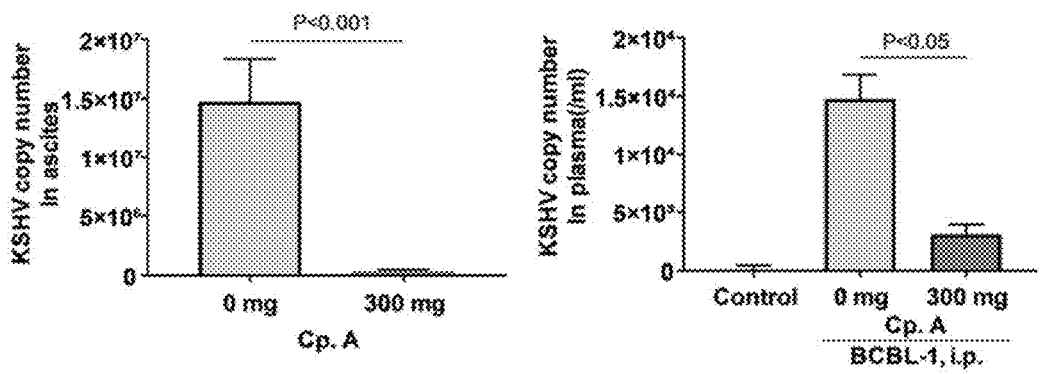
FIG. 6 illustrates an exemplary graph indicating the virus copy number measured in ascites and plasma of PEL mouse models to which the compound A (Cp. A) was administered.

Viruses in ascites and plasma of the above-described mice were detected. Exemplary results thereof are shown in FIG. 6. As illustrated in FIG. 6, the administration of the compound A caused the amount of viruses in ascites and plasma to significantly decrease.

These results indicate that the compound A is effective for treatment of KSHV-associated tumors such as PEL.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for ameliorating, suppressing progression of, and/or treating a tumor caused by a tumor virus, the method comprising the step of:
    administering, to a subject having the tumor, an effective amount of a component that targets a gene product of the tumor virus;
    wherein the tumor virus is Kaposi sarcoma-associated herpesvirus (KSHV),
    wherein the tumor caused by a tumor virus is at least one of Kaposi sarcoma or a KSHV-associated tumor, and
    wherein the component that targets the gene product of the tumor virus is a compound expressed as Formula (II) below, or a pharmaceutically acceptable salt of the compound:

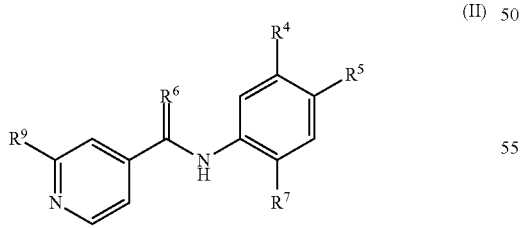

(II)

wherein
$R^4$ represents a hydrogen atom; a halogen atom; a substituted or unsubstituted $C_{1-6}$ alkyl group; a substituted or unsubstituted $C_{2-6}$ alkenyl group; a substituted or unsubstituted $C_{2-6}$ alkynyl group; or a substituted or unsubstituted aryl group,
$R^5$ represents a hydrogen atom; a halogen atom; an amino group; or an azide group,
$R^7$ represents a hydrogen atom; a halogen atom; a diethylamino group; a substituted or unsubstituted nitrogen-containing heterocycloalkyl group; or a substituted or unsubstituted nitrogen-containing heteroaryl group,
$R_8$ represents an oxygen atom or a sulfur atom, and
$R^9$ represents a hydrogen atom; a $C_{1-6}$ alkyl group; or a $C_{2-6}$ alkynyl group.

2. The method according to claim 1,
wherein the compound expressed as Formula (II) 2 or the pharmaceutically acceptable salt thereof, suppresses the expression and/or function of the gene product of the tumor virus.

3. The method according to claim 1,
wherein the gene product is a gene product that is involved in a life cycle of the tumor virus.

4. The method according to claim 1,
wherein the gene product is a gene product whose expression is induced or accelerated at the start of, or during a period of, lytic infection of the tumor virus.

5. The method according to claim 1,
wherein the compound expressed as Formula (II), or the pharmaceutically acceptable salt thereof, suppresses an increase in copy number of the tumor virus.

6. The method according to claim 1,
wherein the component that targets the gene product of the tumor virus is a compound expressed by the following formula, or a pharmaceutically acceptable salt of the compound:

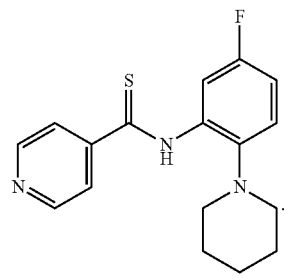 [SMILES: Fc1ccc(N2CCCCC2)c(NC(=S)c2ccncc2)c1]

7. The method according to claim 6, comprising
suppressing growth of the tumor by suppressing the expression and/or function of the gene product of Kaposi sarcoma-associated herpesvirus (KSHV).

8. The method according to claim 7,
wherein the gene product of the tumor virus is RTA.

9. The method according to claim 7,
wherein the gene product of the tumor virus is at least one selected from the group consisting of ORF57, K-bZIP, ORF59, and vIL-6.

10. The method according to claim 7,
wherein the subject is a patient from which at least one selected from the group consisting of Kaposi sarcoma and KSHV-associated tumor is detected.

11. A method for treating a tumor caused by a tumor virus, the method comprising the step of:
    administering, to a subject in need thereof, an effective amount of a compound expressed by the following formula, or a pharmaceutically acceptable salt of the compound:

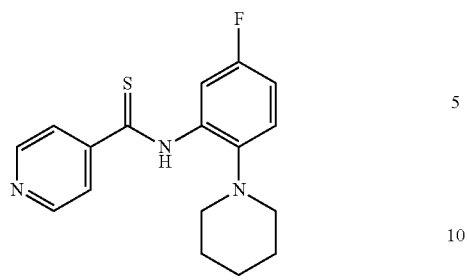
wherein the tumor caused by a tumor virus is at least one selected from the group consisting of Kaposi sarcoma and KSHV-associated tumor, and
wherein the subject is a subject in whom the tumor was detected.
* * * * *